(12) United States Patent
Ramirez Herrera et al.

(10) Patent No.: US 11,185,288 B2
(45) Date of Patent: Nov. 30, 2021

(54) DEVICE AND METHOD FOR MEASURING A PHYSIOLOGICAL PARAMETER OF A HUMAN LIMB

(71) Applicant: KONINKLIJKE PHILIPS N.V., Eindhoven (NL)

(72) Inventors: Sandra Liliana Ramirez Herrera, Eindhoven (NL); Job Lipsch, Eindhoven (NL); Eckhardt Henricus Matheus Schraven, Boxtel (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 375 days.

(21) Appl. No.: 16/315,686

(22) PCT Filed: Jul. 7, 2017

(86) PCT No.: PCT/EP2017/066407
§ 371 (c)(1),
(2) Date: Jan. 7, 2019

(87) PCT Pub. No.: WO2018/007272
PCT Pub. Date: Jan. 11, 2018

(65) Prior Publication Data
US 2019/0298266 A1    Oct. 3, 2019

(30) Foreign Application Priority Data

Jul. 8, 2016    (EP) .................................. 16178683

(51) Int. Cl.
*A61B 5/1455*    (2006.01)
*A61B 5/00*      (2006.01)
(Continued)

(52) U.S. Cl.
CPC ........ *A61B 5/6838* (2013.01); *A61B 5/02416* (2013.01); *A61B 5/14552* (2013.01);
(Continued)

(58) Field of Classification Search
CPC .............. A61B 5/1455; A61B 5/14551; A61B 5/14552; A61B 5/6838; A61B 5/6826; A61B 2560/0443
See application file for complete search history.

(56) References Cited

U.S. PATENT DOCUMENTS 6,154,667 A * 11/2000 Miura ................ A61B 5/14552
                                                   600/323
6,615,064 B1    9/2003 Aldrich
(Continued)

FOREIGN PATENT DOCUMENTS

DE    202005017451    3/2006

Primary Examiner — Eric F Winakur (57) ABSTRACT

The present invention relates to a device for measuring a physiological parameter of a human limb such as peripheral capillary oxygen saturation. The device comprises a body comprising an opening for receiving the limb therein, a moving means coupled to the body and movable relative to the body, a receiving element for receiving a sensor configured for interacting with the limb received in the opening, wherein the body comprises a first section and a second section movable relative to the first section for defining the opening, wherein the moving means is coupled to the second section so as to adjust the size of the opening by moving the moving means.

13 Claims, 5 Drawing Sheets

(51) Int. Cl.
  *A61B 5/024*   (2006.01)
  *A61B 5/145*   (2006.01)
  *A61B 5/318*   (2021.01)

(52) U.S. Cl.
  CPC .......... *A61B 5/6826* (2013.01); *A61B 5/6829* (2013.01); *A61B 5/02438* (2013.01); *A61B 5/14532* (2013.01); *A61B 5/14546* (2013.01); *A61B 5/318* (2021.01); *A61B 2503/045* (2013.01); *A61B 2560/06* (2013.01)

(56) References Cited

U.S. PATENT DOCUMENTS

| | | | |
|---|---|---|---|
| 7,377,794 | B2 | 5/2008 | Abdul-Hafiz |
| 8,412,299 | B2 * | 4/2013 | Kumazaki .......... A61B 5/14552 600/344 |
| 8,721,541 | B2 | 5/2014 | Al-Ali |
| 2007/0078315 | A1 | 5/2007 | Kling |
| 2010/0081900 | A1 | 4/2010 | Price |
| 2013/0131466 | A1 | 5/2013 | Wacogne |
| 2015/0157247 | A1 | 6/2015 | Weinstein |

* cited by examiner

DEVICE AND METHOD FOR MEASURING A PHYSIOLOGICAL PARAMETER OF A HUMAN LIMB

CROSS REFERENCE TO RELATED APPLICATIONS

This application is the U.S. National Phase application under 35 U.S.C. § 371 of International Application No. PCT/EP2017/066407 filed Jul. 3, 2017, published as WO 2018/007272 on Jan. 11, 2018, which claims the benefit of European Patent Application Number 16178683.5 filed Jul. 8, 2016. These applications are hereby incorporated by reference herein.

FIELD OF THE INVENTION

The present invention relates to a device and a method for measuring a physiological parameter of a human limb. In particular, the present invention relates to measuring the oxygen saturation in a non-invasive manner, especially by pulse oximetry on a limb of the human body by use of a pulse oximeter which illuminates the skin and measures changes in light absorption.

BACKGROUND OF THE INVENTION

Pulse oximetry is a technique to assess the peripheral capillary oxygen saturation ($SpO_2$) of blood in a non-invasive manner using an emitted and detected light signal. Typically, a red and infrared light signals are transmitted into the subject's finger by two light-emitting diodes (LEDs), and the scattered light is detected by a photodiode at the other side of the finger, where the blood oxygen saturation is derived from the ratio of pulse amplitudes in the red and infrared light intensity. This utilizes a transmissive method. Alternatively, the LED and the photodiode can be placed on the same side of the finger so as to utilize the reflective method. The light can also be brought to the probe via one or more fibers, for instance one or more optical fibers. In this case, the light source is preferably the end of a fiber. There also may exist pulse oximeters using more than 2 wavelengths, in particular 3, 4, 5, 6, 7 or 8 wavelengths.

Although pulse oximetry is generally measured at the fingertip, other locations on the body are suitable (e.g. forehead, toe, ear lobe). Current probes, however, lack accuracy in their placement after installation, so that the pressure transfer from the device to the limb is not in a well-controlled manner, thereby leading to poor signal stability and contamination of the signal (e.g. measurement signal) by artefacts, such as motion artefacts.

For example, US 2015/0157247A1 discloses techniques for measuring one or more parameters of a subject using a probe having an optical assembly configured and operable for applying optical measurements to a measurement location in a subject and generating optical measured data indicative thereof comprising at least one of pulsatile and occlusion measurements, a pressure system configured and operable for controllably applying pressure to the subject in the vicinity of the measurement location and measuring pressure inside the pressure system and generating pressure data indicative thereof, and a control system configured and operable for receiving and processing the pressure data to identify whether the optical measured data is valid, and for processing the valid optical measured data and determining at least one relation between the valid optical measured data and the corresponding pressure data indicative of at least one parameter of the subject.

A drawback of known probes is the problem of the different sizes in the limbs of infants of different age groups compared to the limbs of adults. The devices known from the past are only suitable for a small range of infants (for non-disposables) and may easily be misplaced by untrained personnel, therefore leading to incorrect results or even finger entrapment during measurement. Also, the optical measurement results delivered by the known devices are affected due to unsatisfactory pressure from the device body to the limb, e.g. finger, due to signal interference and reduced signal stability.

SUMMARY OF THE INVENTION

It is an object of the present invention to provide a device for measuring a physiological parameter of a human limb that enables accurate placement after installation while improving the pressure transfer from the device to the limb as well as increasing the signal stability.

In a first aspect of the present invention a device for measuring a physiological parameter of a human limb is provided that comprises a body comprising an opening for receiving the limb therein, a movable means coupled to the body and movable relative to the body, a receiving element for receiving a physiological sensor configured for interacting light source with the limb received in the opening, wherein the body comprises a first section and a second section dynamic/movable relative to the first section for defining the opening, wherein the moving means is coupled to the second section so as to adjust the size of the opening by moving the moving means.

In a further aspect of the present invention, a method for measuring a physiological parameter of a human limb is provided that comprises the steps of providing a body comprising an opening for receiving the limb therein, wherein the body comprises a first section and a second section movable relative to the first section for defining the opening, providing a moving means coupled to the body and movable relative to the body, providing a receiving element for receiving a physiological sensor for interacting with the limb received in the opening, coupling the moving means to the second section so as to adjust the size of the opening by moving the moving means.

Preferred embodiments of the invention are defined in the dependent claims. It shall be understood that the claimed method has similar and/or identical preferred embodiments as the claimed device and as defined in the dependent claims.

The present invention achieves an improved device for measuring a physiological parameter, in particular $SpO_2$ of blood, of a human limb which can be built with a plurality of alternative designs. The present invention is not restricted to measuring $SpO_2$, but can be applied to measuring other physiological parameters such as pulse rate, dyshaemoglobin fractions (e.g. carboxy-hemoglobin and methemoglobin), electrocardiogram, pulse arrival time and blood sugar. The present invention may be integrated in a pulse oximeter.

In order to perform measurement of physiological parameters, a human limb, e.g. a finger or toe, can be placed to enter the opening of the device body. Preferably, the receiving means comprises, is coupled with or embeds the sensor, which further preferably comprises a light source for generating a measurement light signal and a light detector for detecting the measurement light signal after its interaction with the limb received in the opening of the device body. The light source generates a measurement light signal which interacts with the limb received in the opening and is detected by the light detector. For instance, if the light source is arranged on the same side as the light detector with respect to the received finger (i.e. the angle between the light source and the light detector is zero degree), the measurement is based on reflection of the measurement light signal at the finger. If the light source is arranged on the opposite side to the light detector with respect to the finger (i.e. the angle between the light source and the light detector is 180 degrees), the measurement is based on transmission of the measurement light signal through the finger. Other measurement settings where the angle between the light source and the light detector is between 0 and 180 degrees are possible.

Further, the device according to the present invention is configured with a body that comprises a first section and a second section that is movable relative to the first section. The first section and the second section may be configured as first ring section and section ring section, respectively, to form together a ring, for instance a circular, triangular or quadratic ring.

In addition, the device comprises a moving means which may be coupled to the second section, so that by moving the moving means the second section is moved relative to the first section, thereby changing the size of the opening defined by the first and second sections. The moving means is arranged as a separate entity from the body while being connectable to the second section using a connection element.

The moving means may be configured as a sliding means which is slidable relative to the body, so that by sliding the sliding means the second section is moved relative to the first section to change the size of the opening. Alternatively, the moving means may be configured as a rotating means rotatable relative to the body, so that by rotating the rotating means the second section is moved relative to the first section to change the size of the opening. Further alternatively, the moving means may be configured as a deforming means which is deformable so as move the second section relative to the first section to change the size of the opening.

This differs from the devices known from the past, in particular from the one disclosed in the US patent document mentioned above, where the housing is configured without movable parts and a tray member is configured to slide in order to adjust the size of the cavity to the size of the finger. In the latter, there is no coupling between the tray member and a movable part of the housing so as to adjust the cavity size by sliding.

The present invention enables to improve the stability of the measurement signal since the limb, e.g. the finger, can be placed in a more secure manner within the opening for performing the measurement. In particular, the finger can be more rigidly received against moving or pressing the finger by mistake during measurements, thereby reducing signal interferences of the measurement. Also, the size of the opening can be adjusted effectively to safely receive fingers/toes of different sizes.

Preferably, the moving means, particularly when configured as sliding means, is slidable in a sliding direction, wherein the second section is movable relative to, in particular away from or towards, the first section in the sliding direction. The sliding direction may be in a longitudinal direction of the body. Further preferably, the sliding means is coupled to the second section at a joint position of the body so that the sliding means stays still with respect to at least the joint position while sliding.

In a preferable embodiment, the moving means is detachable, preferably entirely detachable, from the body. The moving means can be entirely detached from the body of the device, so that there is no connection between the body and the moving means. Advantageously, the body and the moving means can be more easily replaced if one of them is defect.

In another preferable embodiment, the body comprises a flexible section opposite to the second section with respect to the first section, the flexible section being movable relative to the first section. The flexible section is connected to the first section, thereby providing an effective grip. In particular, the flexible section is preferably made of an elastic material, so that the flexible section tends to return to its released state due to the elasticity. Also, due to its elasticity, the flexible section is able to absorb forces wrongly applied to the body so that the measurement signal remains stable.

In a further preferable embodiment, the flexible section comprises a press surface for pressing in order to slide the moving means, wherein the press surface comprises preferably a convex surface when no external force is applied to the press surface. The moving means is therefore coupled to the flexible section and to the second section simultaneously. This strengthens the coupling between the body and the moving means, so that the adjustment of the size of the opening is more effective. A convex press surface is advantageous for sliding the moving means since it improves the sensibility of the press surface e.g. over a planar surface, so that the user can find the proper surface to press in order to slide the moving means without the need of visual contact to the press surface. Further preferably, the body has a mushroom-like cross-section along its longitudinal direction between the flexible section and the second section. The flexible section may form a second opening with the first section.

Alternatively, a front and/or a rear surface may be provided to cover the spacing between the flexible section and the first section. Further alternatively, the flexible section may be configured to extend from the first section to the top of the body opposite to the second section to form a closed surface between the first section and the top of the body. In this way, erroneous use of the device, e.g. inserting a finger into a wrong opening, as well as misplacement of the device may be prevented.

In a further preferable embodiment, the flexible section is configured to extend laterally beyond the first section to form two concave surfaces for supporting the body. The concaves surfaces are advantageous for gripping the device, in particular using three fingers, so that the device can be more easily held with increased stability. Preferably, the concave surfaces can be advantageously used for supporting the body while pressing the press surface, in particular using three fingers including two fingers supporting from below the concave surfaces and one finger onto the press surface of the flexible section.

Preferably, a rigid side part is provided to maintain the concave form of the concave surfaces. In particular, the rigid side part may have a form that corresponds to the concave surfaces of the flexible section, so that the concave form can be maintained more effectively. Alternatively or additionally, the rigid side part is integrated to the moving means, so that when the moving means is coupled to the body, the rigid side part is preferably in direct or indirect contact with the concave surfaces.

In a further preferable embodiment, the moving means is arranged on a rear side of the body opposite to a front side for receiving the limb. This facilitates the optical measurement since the entering of the limb such as finger is not hindered by the moving means.

In a further preferable embodiment, the device is operable in a closed state in which the second section is released and an open state in which the second section is moved away from the first section by sliding the moving means. The device can be effectively operated to conduce optical measurements of physiological parameters.

In a further preferable embodiment, the second section comprises, preferably is made of, an elastic material such as a silicone-like and/or a rubber-like material, further preferably silicone-rubber, so that when the device is in the released state, the second section is reset to close the opening. In this way, the second section is able to automatically close the opening whenever it is released from external forces or when the magnitude of external forces applied to move the second section away from the first section are below a threshold value. The limb can be securely received by the device. This is particularly advantageous when measurements are performed at limbs of small sizes, such as fingers of infants.

In a further preferable embodiment, the moving means comprises a first (e.g. top) part and a second (e.g. bottom) part for being inserted into the body. The moving means may further comprise a third (e.g. middle) part arranged between the first and the second part. In particular, the first part of the moving mans, particularly when configured as sliding means, can be inserted into a top section of the body (e.g. the flexible section) that is opposite to the second section with respect to the first section. In this way, the moving means can be slit by pressing the top section, e.g. the flexible section, of the body so that the pressure is transferred to the moving means via its first part. The second part of the moving means can be inserted into the second section. The optional third part is preferably configured as a longitudinal board connecting the first part with the second part of the moving means. Alternatively, the body of the device can be casted around the other parts.

In a further preferable embodiment, the sensor is arranged at, preferably embedded into, the second part of the moving means. In particular, at least one of the light source and the light detector can be arranged at, preferably embedded into the third part of the moving means.

In a further preferable embodiment, a guiding means for guiding the moving means when sliding is attached to the body. In this way, the sliding movement of the moving means is a guided movement so that the adjustment of the size of the opening for receiving a limb is more controllable. The sensor may be arranged at, preferably embedded into the guiding means. In particular, at least one of the light source and the light detector can be arranged at, preferably embedded into the guiding means. Preferably, the guiding means is a part of the device, so that the device is configured in a three-part form.

In a further preferable embodiment, the guiding means is insertable into a recess of the first section and/or is arranged to engage the moving means, preferably a middle part of the moving means, the recess being preferably arranged on a top side of the first section opposite to the second section with respect to the first section. In this way, the guiding means can be safely coupled to the body of the device and/or the moving means. The guiding means has preferably two protrusions on the rear side of the body, between which the middle part of the moving means is guided while sliding the moving means. Alternatively, the body can be casted around the guiding and moving means. Alternatively or additionally, the guiding means can be replaced by varying the density of the body by changing the wall thickness surrounding, preferably the first section. Therefore this section will not deform and work as a guide.

In a further preferable embodiment, the sensor is arranged at, preferably embedded into, the first section and/or the second section. In particular, one of the light source and the light detector is embedded in the first section, while the other one of the light detector and the light source is embedded in the second section, thereby facilitating the measurement based on light reflexion.

BRIEF DESCRIPTION OF THE DRAWINGS

These and other aspects of the invention will be apparent from and elucidated with reference to the embodiments described hereinafter. In the following drawings

DETAILED DESCRIPTION OF THE INVENTION

Pulse oximetry is the technique to assess the oxygen saturation ($SpO_2$) of blood in a non-invasive manner. Since its introduction in the clinic in the 1980's, it has become a standard of care in various clinical settings. A pulse oximeter probe is usually applied to a fingertip. Red and infrared light is generated by a light source, for instance by two light-emitting diodes (LEDs), and transmitted into the tissue, and the scattered light is recorded by a light detector, for instance by a photodiode at the other side of the finger. The cardiac-induced pulsations in the blood volume manifest themselves as pulsations in the detected light intensity. The oxygen saturation is derived from the ratio of pulse amplitudes in the red and infrared light intensity, where the relationship results from a difference in color of oxygen-bound and oxygen-unbound hemoglobin.

The most ideal location to obtain a pulse oximetry signal is the finger tip or toe because the pulsatile optical signal is very strong on these locations, and the body site is easy to access. There are three types of mechanisms of attachment of pulse oximetry probes for fingers and toes. These probes operate preferably in a transmission geometry, where the detector and the emitter are at opposite sides of the finger.

For children, the size of the fingers and toes is significantly smaller compared to those of adults, so that special probes need to be designed to be suitable for these smaller sizes. For these designs it has not yet been realized to make a single probe that can fit on both large and small fingers and toes.

Further, the devices known from the past are insufficient in terms of stability of the measurement signal. In particular, the signal interference, e.g. caused by wrongly holding the device or pressing the finger or toe leading to erroneous pressures transferred to the sensor, remains high so that the measured physiological parameters are not reliable.

The invention solves the above problems by providing a device with improved positioning of the limb in the opening defined by the first and second sections of the body.

Without limiting the present invention, the following exemplarily embodiments will be described in detail in the following by referring to a moving means that is configured as sliding means. However, it is noted that the following description also holds and the technical effects of the invention may also be achieved for other embodiments in which the moving means is configured differently, e.g. as rotating means or deforming means.

FIGS. 1A-1C show a first embodiment of a device 10 according to the invention in three different perspective views. The device 10 comprises a body 12 and a sliding means 14 (representing a non-limiting embodiment of moving means). The body 12 comprises a first section 18 and a second section 20, which is here preferably arranged as an extension of the first section 18 in a longitudinal direction of the body 12. The first section 18 and the second section 20 define an opening 16 between each other for receiving a limb (not shown), such as a finger of a patient.

As shown in the perspective views of FIGS. 1B and 1C, the device 10 has a front side 40 and a rear side 38 opposite to the front side 40, wherein the sliding means 14 is attached to the body 12 from the rear side 38. As will be shown in more detail below, the sliding means 14 can be slit along a sliding direction, preferably the longitudinal direction of the body 12 relatively to the body 12. The second section 20 is movable relative to the first section 18, preferably along the sliding direction of the sliding means 14.

Preferably, the second section 20 is made of an elastic material so that it can be deformed by pulling downwards, thereby enlarging the opening 16 leading to an open state of the device 10, and reset to close the opening 16 thereby leading to the (original) closed state of the device 10. The sliding means 14 is coupled to the second section 20 so as to adjust the size of the opening 16 by sliding the sliding means 14. While sliding, the sliding means 14 stays still with respect to a joint position of the second section 20 at which the sliding means is coupled to the second section 20.

Further preferably, as can be seen in FIG. 1C, the sliding means 14 is configured to form a back wall to the opening 16 on the rear side 38 so that the depth of insertion of a limb, e.g. a finger, is limited to the distance between the front side 40 and the sliding means 14.

Further preferably, the device 10 further comprises a guiding means 46 for guiding the sliding movement of the sliding means 14. The guiding means 46 preferably comprises two protrusions on the rear surface 38 of the body 12, for instance at the height of the first section 18 as shown in FIG. 1C, wherein the protrusions are configured to engage the sliding means 14. In FIGS. 1A-1C, the sliding means 14 and the guiding means 46 are attached to the body 12. Preferably, all three parts, namely the body 12, the sliding means 14 and the guiding means 46, are configured so that the device 10 does not function without any of them. This is advantageous for effective controlling of the device 10 to avoid wrong mounting or measurement operation that may lead to erroneous measurement results.

Figure 2:
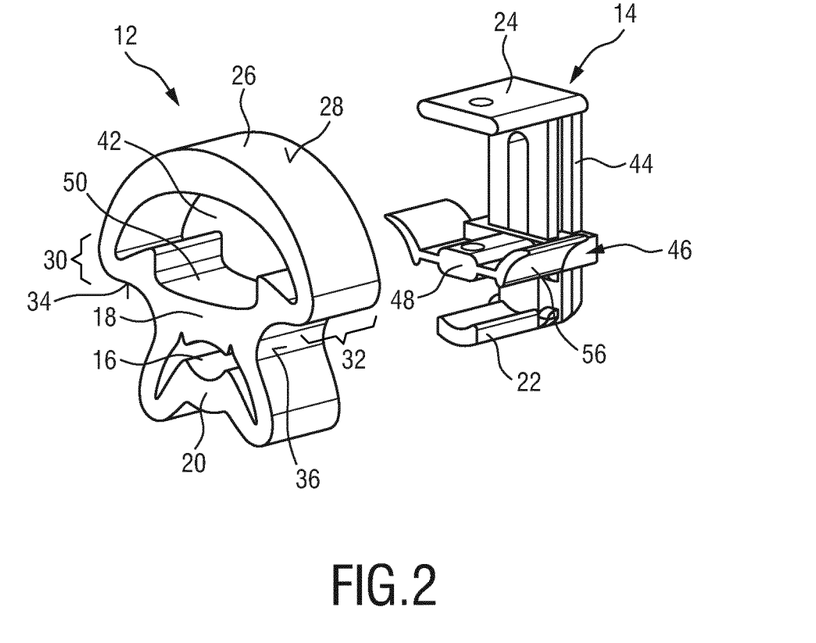
FIG. 2 shows the device of FIG. 1, wherein a sliding means of the device is detached from a body of the device.

FIG. 2 shows an explosive view of the device 10 of FIG. 1. Here, the sliding means 14 and the guiding means 46 are detached from the body 12.

In the exemplary embodiment shown in FIG. 2, the body 12 further comprises a flexible section 26 opposite to the second section 20 with respect to the first section 18, the flexible section 26 being movable relative to the first section 18. The flexible section 26 extends from the top side of the body 12 towards the top side where the first section 18 is arranged. The flexible section 26 is configured as an extension of the first section 18 towards the top side. Further, the flexible section 26 comprises a convex press surface 28 facing upwards for pressing in order to slide the sliding means 14, e.g. using a finger. Preferably, the flexible section 26 is made of an elastic material so that it can be deformed by pressing downwards and reset to the convex form when released from the pressure. In the exemplary embodiment shown in FIG. 2, the flexible section 26 and the first section 18 form in between themselves an additional opening 42.

Further, the flexible section 26 is configured to form two concave surfaces 34, 36 each on one of two side portions 30, 32 of the body 12 and facing downwards for supporting the body 12, e.g. using two fingers. In this way, the device 10 can be held using three fingers. The flexible section 26, the first section 18 and the second section 20 are preferably configured to enable a mushroom-like form.

The sliding means 14 preferably comprises a top part 24, a middle part 44 and a bottom part 22, the middle part 44 being arranged between the top part 24 and the bottom part 22. The top part 24 is configured to insert into a top section of the body 12, preferably the flexible section 26, while the bottom part 22 of the sliding means 14 is configured to insert into the second section 20. The middle part 44 is preferably configured as a longitudinal board.

The guiding means 46 is configured to engage the sliding means 14, preferably the middle part 44. As can be seen in FIG. 2 and without limiting the present invention, the middle part 44 comprises a guiding track on its two longitudinal edges. The guiding means 46 is configured to engage the middle part 44 preferably in a form-locking manner so that the guiding means 46 is slidable along the middle part 44. The guiding means 46 is further preferably configured to insert into the body 12 at the height of the first section 18, wherein two rigid side parts 56 are preferably provided to maintain the concave form of the concave surfaces 34, 36 of the body 12 when the guiding means is 46 is inserted into the body 12. The additional opening 42 is configured to allow sufficient space for sliding and prevent excessive pressure on the first section 18 when the device 10 is being open (i.e. when the opening 16 is being enlarged by the sliding motion). Further preferably, a recess 50 is formed on the top side of the first section 18. A central portion 48 of the guiding means 46 is arranged between the two rigid side parts 56.

Figure 1:
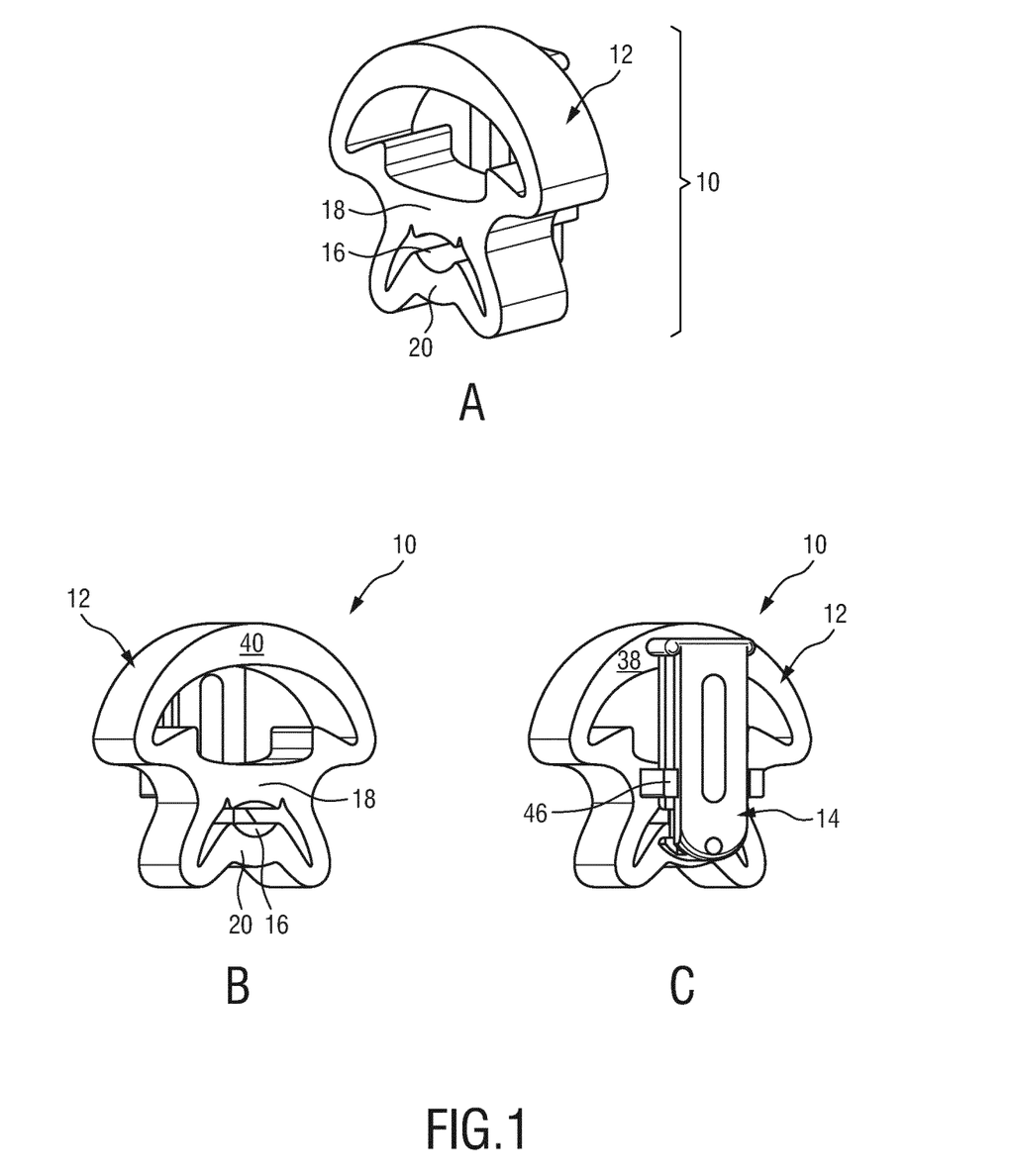
FIGS. 1A to 1C show a first embodiment of a device according to the invention in three different views.
Figure 3:
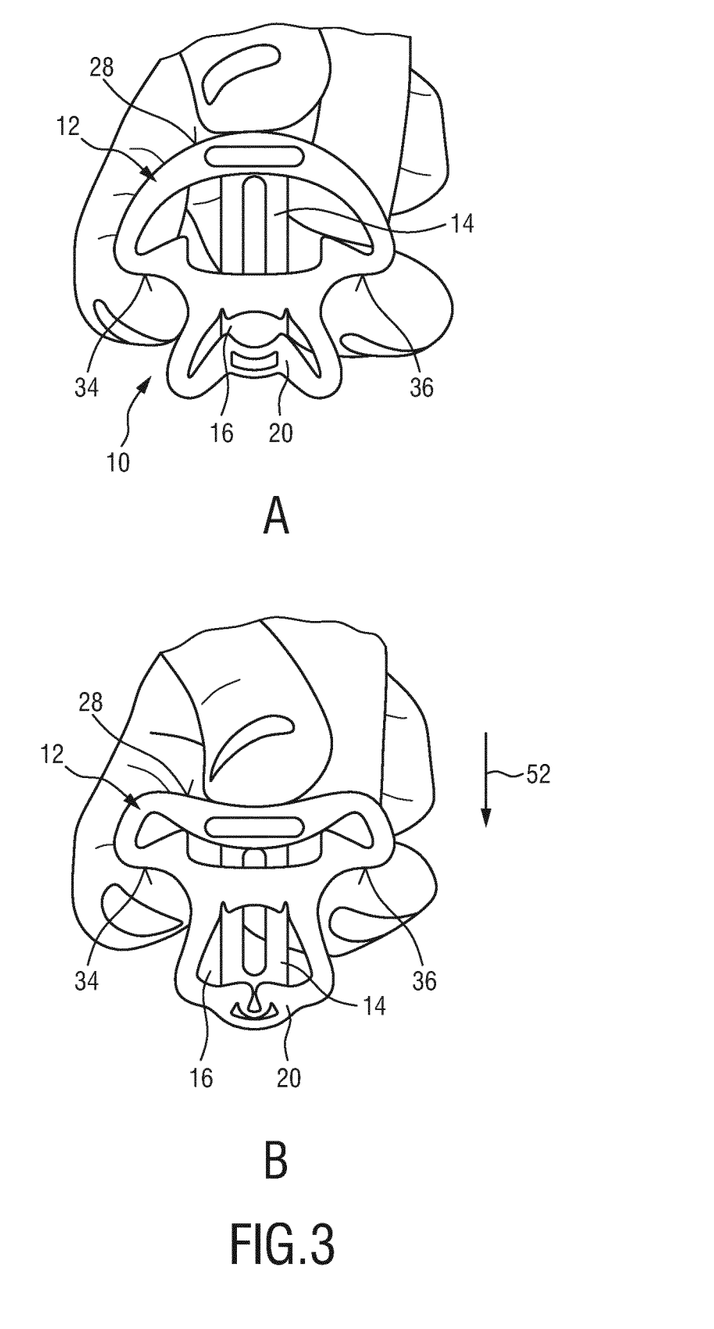
FIG. 3A shows the device of FIG. 1 in a closed state.
FIG. 3B shows the device of FIG. 1 in an open state.

Although not shown in FIGS. 1-3, the device 10 further comprises a receiving element for receiving a sensor, the sensor comprising a light source for generating a measurement light signal and a light detector for detecting the measurement light signal after its interaction with the limb received in the opening. In this way, physiological parameters such as $SpO_2$ can be measured for the limb.

For instance, the sensor may be embedded into the body 12, the sliding means 14 and/or the guiding means 46. In particular, for performing optical measurements in a transmission geometry, one of the light source and the light detector may be embedded into the first section 18 or the guiding means 46 (e.g. the central portion 48) while the other one of the light source and the light detector may be embedded into the second section 20 or the bottom part 22 of the sliding means 14. In this way, the light source and the light detector are arranged on two opposite sides with respect to the opening 16 and consequently with respect to a limb received by the opening 16.

For performing optical measurements in a reflexion geometry, both the light emitter and the light detector are arranged in the first section 18, the second section 20, the bottom part 22 of the sliding means 14 or the guiding means 46 (e.g. the central portion 48). In this way, both the light source and the light detector are arranged on the same side with respect to the opening 16 and consequently with respect to the limb received by the opening 16.

Preferably, since the sensor is embedded within the body 12, the sliding means 14 and/or the guiding means 46, the sensor can be better protected by reducing or avoiding dirt or external pollution within the opening which may interfere with the sensor. Embedding all parts in a single element, prevents external elements not only to interfere with the signal but also keeps the mechanism protected from getting clog.

FIG. 3A shows the device 10 being held in the closed state. As can be seen in FIG. 3A, the device 10 is held by three fingers, two supporting the body 12 from below the concave surfaces 34, 36 and one touching the press surface 28 of the flexible section 26 from the top side. No pressure is applied to the press surface 28 so that the second section 18 is reset to close the opening 16. In this state, the opening 16 may be completely closed (i.e. the second section 20 form-lockingly touches the first section 18 from below) or be closed to a minimum opening size.

FIG. 3B shows the device 10 being operated in the open state. As can be seen in FIG. 3B, the device 10 is held while a pressure is applied to the press surface 28 from the top side downwards as indicated by an arrow 52. This pressure is transferred to the sliding means 14 via the top part 24 of the sliding means 14 which is inserted into the flexible section 26 of the body 12, thereby leading to a sliding movement of the sliding means 14 along the longitudinal direction indicated by the arrow 52. The sliding movement of the sliding means 14 is guided by the guiding means 46 as described in conjunction with FIG. 2 above.

Since the sliding means 14 is further coupled to the second section 20, the latter is thereby moved downwards so as to enlarge the size of the opening 16. During the application of the pressure, the two fingers supporting the body 12 at the two concave surfaces 34, 26 serve as a resistance which prevents the body 12 of the device 10, in particular the first section 18, from moving downwards. This can be further facilitated by the rigid side parts 56 or alternatively by changing the density of the material used for the side portions 30, 32 for maintaining the form of the concave surfaces 34, 36. In this way, any limb such as finger or toe having a size that is smaller or equal to the opening 16 in the open state of the device 10 can be received by inserting into the opening 16 from the front side 40 of the device 10. After the limb has been received in the opening 16 and its position within the opening 16 has been adjusted, the pressure can be released from the press surface 28. The second section 20 than is reset to close the opening 16, thereby applying resetting forces to tighten the received limb so as to enable safe attachment of the device 10 to the limb. Alternatively or additionally, the inner surface of the opening 16 facing the limb to be received is configured so, e.g. as an anti-friction surface, that the device 10 can be prevented from sliding off the limb, such as finger or toe.

Preferably, the device 10 may be provided with different resetting forces depending on the size of the opening 16 in the open state. For instance, the resetting force may be smaller for limbs of smaller sizes, e.g. fingers of neonates, which have a lower central venous pressure and weaker fingers, compared to children or adults. The elastic material, of which the body 12, in particular the second section 20 and/or the flexible section 26 are made of, may comprise silicone or silicone rubber.

Instead of using the guiding means 46 to guide the sliding means 14, the guiding means 46 may be omitted so that the device 10 comprises only the body 12 and the sliding means 14 (two-part form). In order to guide the sliding means 14 while sliding, the body 12 is preferably built to have a varying density so that first section 18 is rigid against sliding movement of the sliding means 14.

As can be seen in FIGS. 3A-B, the device 10 can be held using only three fingers which touch the body 12 without touching the sliding means 14 or the guiding means 46.

During the measurement, if the limb, e.g. finger, inside the opening 16 is pressed downwards, it is achieved that the device 10 does not open. In this way, signal interferences of the measurement is reduced over the devices known from the past. When the finger is press downwards, the reacting force of the surface will be applied on the bottom of the second section (20) along with the sliding (14), which will push upwards the limp (finger) on the opening (16) and at the same time the limp (finger) will push upwards the first section (18). Everything will be move upwards without changing the pressure on the limp (finger). Since there is no resistance on 36 and 34, the probe will not open. Further, it is also achieved that the pressure onto both ends of the sensor is not increased. Another advantage is associated with the way the device 10 is opened: pressure needs to be applied to the press surface 28 in order to bring the device 10 into the open state. This is requirement provides an obstacle to open the device 10 thereby preventing the device 10 from being mistakenly used, e.g. by small children.

Also, the chance of entrapment of the limb such as finger is reduced compared to devices known from the past. In particular, the first section 18 and the second section 20 may be made of soft elastic material such that even larger fingers will not get trapped after being received in the opening 16. This elastic material together with the depth limitation using the back wall of the sliding means 14 (see FIG. 1C above) reduces the entrapment risk significantly even further.

When the device 10 is attached to the finger as described above (see FIG. 3B), the position of the finger and consequently the resetting force that is applied to the finger is more stably maintained compared to known devices since by arranging the opening 16 within the length of the sliding means 14, the device 10 according the present invention is more rigid against external forces. In particular, once pressures are applied from outside the device 10 to the device 10 (e.g. a first grapping the device 10 from the outside while compressing the device 10 or a grasping motion), such pressures are not transferred directly to the finger and the sensor affecting the measurement. When the device is held from the outside and it is not held such that resistance is created on 34 and 36, the pressure is applied on the sliding means (14) in particular on 24 and 22 not affecting the pressure on the limb (finger) nor tightening or opening the probe.

Figure 4:
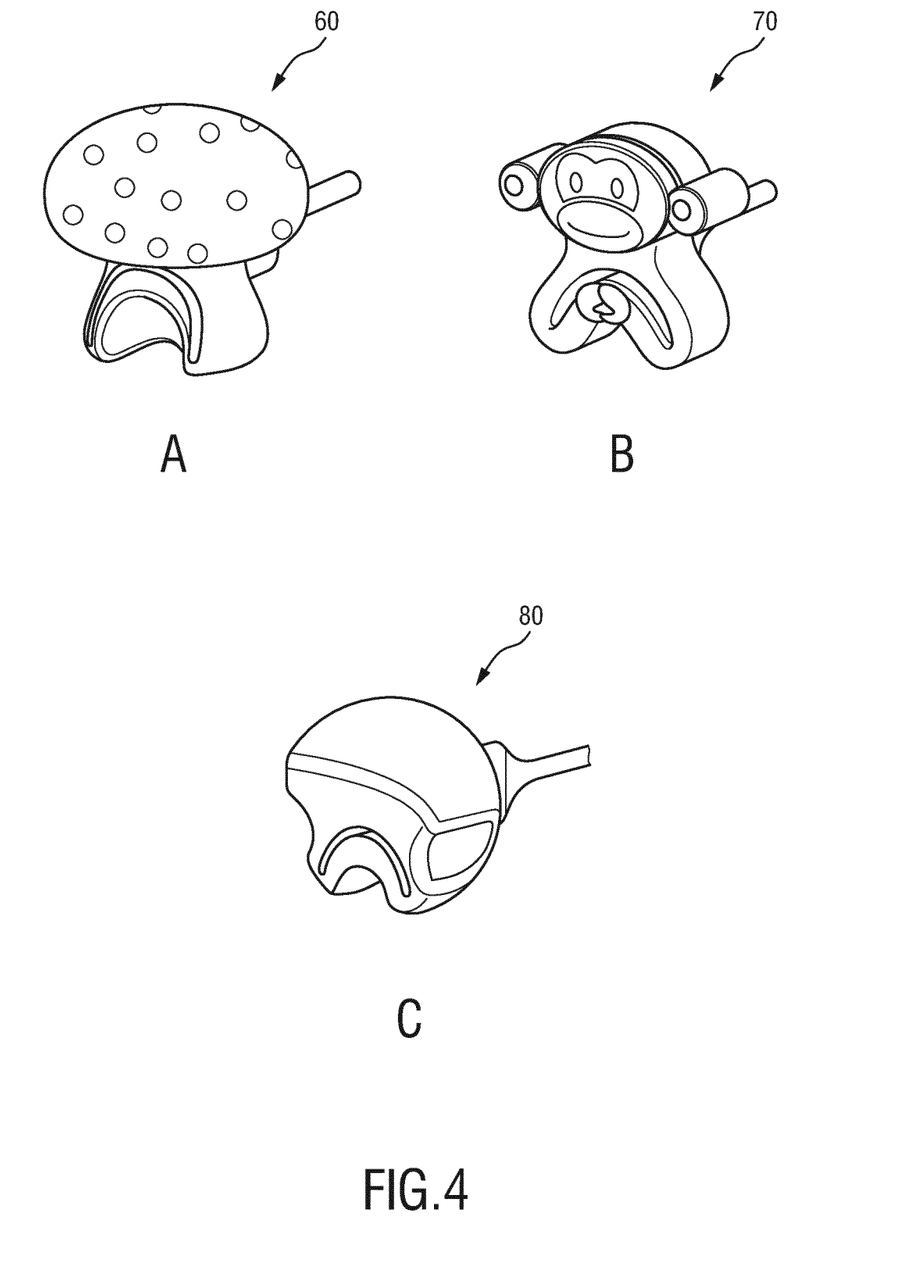
FIGS. 4A-C show a second, a third and a fourth embodiment of a device according to the invention.

FIGS. 4A-4C show three additional embodiments of the device 60, 70, 80, respectively. In all these embodiments, the device 60, 70, 80 are similar to that of FIG. 1 except that the flexible section 26 is configured to extend from the first section to the top of the body 12 opposite to the second section 20 to form a closed surface between the first section 18 and the top of the body 12. In this way, erroneous use of the device 60, 70, 80, e.g. inserting a finger into a wrong opening (e.g. the additional opening 42 shown in FIG. 2), as well as misplacement of the device may be prevented.

Figure 5:
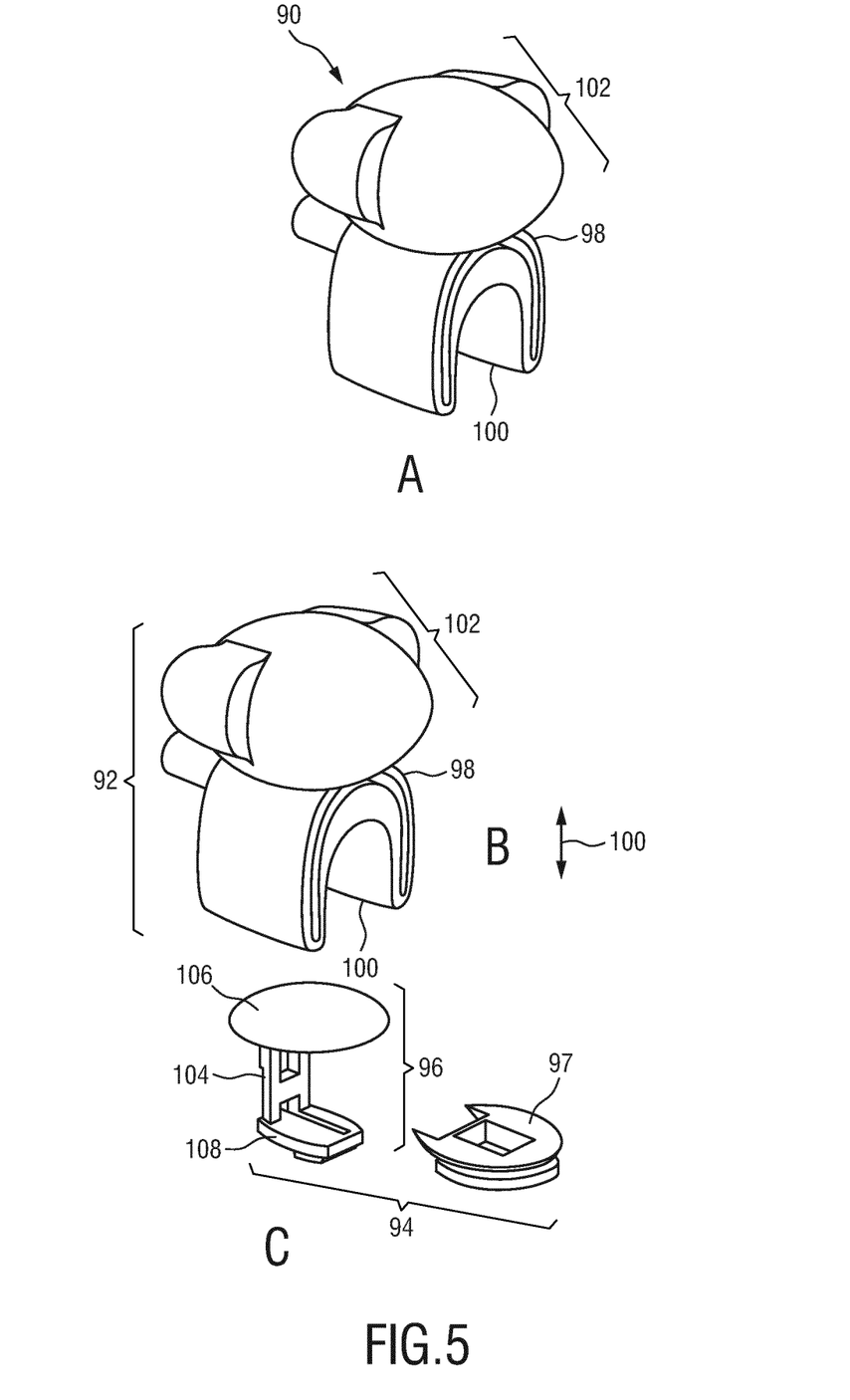
FIGS. 5A-C show a fifth embodiment of a device according to the invention.

FIGS. 5A-5C show a fifth embodiment of the device 90. In this embodiment, the device 90 comprises a flexible body 92, which is shown separately in FIG. 5B, and a rigid arrangement 94 which is shown separately in FIG. 5C. The flexible body 92 comprises a first section 98 and a second section 100, which is movable along a longitudinal direction 110 indicated by an arrow relative to the first section 98. In this way, an opening (not explicitly shown in FIGS. 5A-C) can be formed between the first and the second section for receiving a limb such as finger or toe. The flexible body 92 further comprises a top section 102 similar to the embodiments shown in FIGS. 4A-C and opposite to the second section 100 with respect to the first section 98. The second section 100 is preferably elastic so that it is reset to close the opening when no external force is applied to the flexible body 92.

As can be seen in FIG. 5C, the rigid arrangement 94 comprises a sliding means configured as a rigid plunger section 96. The plunger section 96 comprises a middle part 104 arranged between a top part 106 and a bottom part 108. The rigid arrangement 94 further comprises a guiding means configured as a rigid holder section 97 that can be slidably attached to the middle part 104 of the plunger section 96.

The rigid plunger section 96 is configured to house electronic elements which preferably includes a USB cable when used with the reflective measurement geometry. The rigid holder section 97 is configured to create the touching surface for the limb. Together with the plunger section 96, the holder section 97 determines the adjustment range of the size of the opening for different limb sizes. The holder section 97 may also be configured to hold secondary electronics to have LEDs and a photovoltaic (PV) cell on opposite sides of the limb. The flexible body 92 is configured to hold both the rigid plunger section 96 and the rigid holder section 97. Further, the flexible body 92 may also be configured to provide visual usage feedback and create good and correct hold.

In FIG. 5A, the device 90 is shown in a view where the flexible body 92 and the rigid arrangement 94 are assembled. In particular, the top part 106 of the plunger section 96 is attached to the top section 102 of the flexible body 92, wherein the bottom part 108 of the plunger section 96 is attached to the second section 100 and the holder part 97 is attached to the first section 98.

In this way, the plunger section 96 can be slit relative to the holder part 97 by pressing the flexible top section 102 of the flexible body 92, thereby moving the second section 100 away from the first section 98, so that the size of the opening for receiving a limb can be enlarged.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

Any reference signs in the claims should not be construed as limiting the scope.

The invention claimed is:

1. A device for measuring a physiological parameter of a human limb, comprising:
    an elastic body comprising a first section and a second section which together form a ring and define an opening for receiving the limb therein;
    a slider coupled to the body and movable relative to the body; and
    a physiological sensor configured for interacting with the limb received in the opening;
    wherein the second section of the body is movable relative to the first section for defining the opening, wherein the slider is coupled to the second section of the body so as to adjust a size of the opening by moving the slider;
    wherein the slider is detachable from the body; and
    wherein the slider is coupled to the second section at a joint position of the second section, wherein the slider is configured to stay still with respect to the joint position while being slid.

2. The device according to claim 1, wherein the body comprises a flexible section opposite to the second section, the flexible section being movable relative to the first section.

3. The device according to claim 2, wherein the flexible section:
    comprises a press surface for applying an external force in order to move the slider, wherein the press surface comprises a convex surface when no external force is applied to the press surface; or
    is configured to extend laterally beyond the first section to form two concave surfaces for supporting the body.

4. The device according to claim 1, wherein the slider is arranged on a rear side of the body opposite to a front side for receiving the limb.

5. The device according to claim 1, wherein the device is operable in a closed state in which the second section is released from external forces and an open state in which the second section is moved away from the first section by moving the slider.

6. The device according to claim 5, wherein the second section is made of silicone or rubber, so that when the device is in the closed state, the second section is reset to close the opening.

7. The device according to claim 1, wherein the slider comprises a first part and a second part for being inserted into the body.

8. The device according to claim 7, wherein the second part is configured to be inserted into the second section, the first part being configured to be inserted into a flexible section of the body opposite to the second section.

9. The device according to claim 7, wherein the physiological sensor is:
    arranged at the second part of the slider, or arranged at the first section or the second section.

10. The device according to claim 1, further comprising a guide attached to the body, wherein the guide is for guiding the slider when moving.

11. The device according to claim 10, wherein the guide is insertable into the first section or is arranged to engage the slider.

12. The device according to claim 1, wherein the physiological sensor comprises a light source for generating a measurement light signal and a light detector for detecting the measurement light signal after its interaction with the limb received in the opening.

13. A method for manufacturing a device for measuring a physiological parameter of a human limb, comprising the steps of:
- providing an elastic body comprising a first section and a second section which together form a ring and define an opening for receiving the limb therein, wherein the second section is movable relative to the first section for defining the opening;
- providing a slider coupled to the body and movable relative to the body;
- providing a physiological sensor configured for interacting with the limb received in the opening;
- coupling the slider to the second section so as to adjust a size of the opening by moving the slider;
- wherein the slider is detachable from the body;
- wherein the method further comprises providing the slider coupled to the second section at a joint position of the second section, wherein the slider is configured to stay still with respect to the joint position while being slid.

* * * * *